United States Patent [19]
Stephen et al.

[11] Patent Number: 5,779,661
[45] Date of Patent: Jul. 14, 1998

[54] METHOD OF TREATING DYSFUNCTIONAL BLADDER SYNDROMES BY ELECTROMOTIVE DRUG ADMINISTRATION

[75] Inventors: Robert L. Stephen, Salt Lake City, Utah; Manfred Stöhrer, Murnau, Germany; Umberto Fontanella, Milan, Italy; Donald P. Griffith, Houston, Tex.; Franco Lugnani, Trieste, Italy; Cino Rossi, Rome, Italy; Silvio Eruzzi, Mantova, Italy

[73] Assignee: Physion, S.r.l., Italy

[21] Appl. No.: 570,507

[22] Filed: Dec. 11, 1995

[51] Int. Cl.$^6$ ............................................. A61N 1/30
[52] U.S. Cl. .................................... 604/21; 604/49
[58] Field of Search ................... 604/21, 28, 49, 604/54–5, 264; 607/3, 40–41, 72, 75, 115–16, 143

[56] References Cited

U.S. PATENT DOCUMENTS

| | | | |
|---|---|---|---|
| 4,411,648 | 10/1983 | Davis et al. | 604/21 |
| 4,744,787 | 5/1988 | Phipps et al. | 604/20 |
| 4,747,819 | 5/1988 | Phipps et al. | 604/20 |
| 4,752,285 | 6/1988 | Petelenz et al. | 604/20 |
| 4,878,892 | 11/1989 | Sibalis et al. | 604/20 |
| 5,002,956 | 3/1991 | Thiel | 514/297 |
| 5,147,294 | 9/1992 | Smith et al. | 604/49 |
| 5,167,616 | 12/1992 | Haak et al. | 604/20 |
| 5,222,936 | 6/1993 | Stephen et al. | 604/20 |
| 5,232,441 | 8/1993 | Stephen et al. | 604/49 |
| 5,234,408 | 8/1993 | Griffith | 604/93 |
| 5,236,413 | 8/1993 | Feiring | 604/21 |
| 5,301,688 | 4/1994 | Stephen et al. | 604/20 |
| 5,328,451 | 7/1994 | Davis et al. | 604/20 |
| 5,401,239 | 3/1995 | Stephen et al. | 604/21 |
| 5,486,160 | 1/1996 | Rossi et al. | 604/21 |

FOREIGN PATENT DOCUMENTS

| 3809814C1 | 9/1989 | Germany | A61K 31/435 |
|---|---|---|---|

OTHER PUBLICATIONS

Fontanella, U.A., et al. "Iontophoretic Local Anaesthesia for Bladder Dilatation in the Treatment of Interstitial Cystitis", Br. J. Urol. Jun. 1992, 69(6) 662–3.

Ramahi, A.J., et al. "A Practical Approach to the Painful Bladder Syndrome," J. Reprod. Med. Obstet. Gynec. 1990 35(8) 805–809.

Nurmi, M. et al. "Evaluation of Upper and Lower Urinary Tracts After Camey Operation," Scand. J. Urol. Nephrol. 1989 23(4) 275–277.

Lugnani, F. et al. "Iontophoresis of Drugs in the Bladder Wall: Equipment and Prelim. Studies," Artif. Organs. 17(1) 8–17, 1993.

Dranov, Paula: "The Woman's Disease Doctors Misdiagnose", Good Housekeeping, Aug. 1995 pp. 82–83, 135.

Petelenz, J.A. et al.: "Iontophoresis of dexamethasone: laboratory studies", Journal of Controlled Release, 20 (1992) pp. 55–66.

Brown, Joan Heller: "A tropine, Scopolamine, And Related Antimuscarinic Drugs", The Pharmacological Basis of Therapeutics, Eight Edition, Pergamon Press. pp. 150–159.

Zamula, Evelyn: "Interstitial Cystitis: Progress Againt Disabling Bladder Condition"; FDA Consumer, Nov. 1995 pp. 28–30.

Primary Examiner—Mark Bockelman
Assistant Examiner—Ellen S. Tao
Attorney, Agent, or Firm—Jacobson & Johnson

[57] ABSTRACT

An intravesical method of treating dysfunctional bladder syndromes by Electromotive Drug Administration (EMDA) of local anaesthetic drugs, anti muscarinic drugs and sympathomimetic agents. The administration of said drugs combined with hydraulic bladder dilatation causes relaxation of the detrusor muscle, reversing the hypertonicity associated with dysfunctional bladder syndromes.

15 Claims, 3 Drawing Sheets

METHOD OF TREATING DYSFUNCTIONAL BLADDER SYNDROMES BY ELECTROMOTIVE DRUG ADMINISTRATION

BACKGROUND OF THE INVENTION

The present invention relates to a method of treating multiple pathophysiological conditions of the bladder, herein termed dysfunctional bladder, by means of Electromotive Drug Administration (EMDA).

As it is known in the art, stimulation of the parasympathetic nerves causes contraction of the detrusor muscle and relaxation of the sphincter: the person voids the urine contained in his/her bladder. Stimulation of the sympathetic nerve supply causes contraction of the sphincter: the person retains the urine in his/her bladder.

Lesions or disturbances in function anywhere along the autonomic nervous system (ANS) pathways leading from the brain to the detrusor and sphincter (of the bladder) may cause disturbances of micturition. Some examples include: Parkinson's disease, "stroke" and cerebral tumors; quadriplegia and paraplegia, whether traumatic or disease-induced and spina bifida; lesions of the sacral outflow nerves or of the pelvic nerves; neuromuscular "imbalance" within the bladder wall and hypertonicity of the detrusor.

Although the disorders listed herein above comprise only a fraction of those which may give rise to a dysfunctional bladder, the list emphasizes that the origins of these disturbances may arise in widely separated anatomic regions. Sometimes the urologic disorders so caused are minor, often they are of grave clinical significance. Whether the bladder exhibits severe permanent spasm or flaccidity, there often follows obstruction of urinary outflow and the need for a permanent indwelling bladder catheter leading to infections, kidney stones and terminal failure of the kidneys. Many patients with quadriplegia and paraplegia require dialysis (artificial kidney) treatments because of this chain of events.

Known in the art are many drugs available for systemic administration (by mouth or by injection) that promote or inhibit micturition. Sometimes these drugs are administered specifically for their actions upon the bladder but more often they are used to treat some other malady and their urologic actions are an annoying side effect.

It is known that the parasympathetic nerves have a more profound effect upon the bladder than does the sympathetic nervous system, therefore, the majority of drugs available for use in this field are either parasympathomimetic or parasympatholytic in their action.

Of all the parasympatholytic drugs available, those relevant to this invention are termed antimuscarinic drugs because their actions block those of the naturally occurring parent alkaloid, muscarine, which mimics the action of ACh upon its receptors innervated by post ganglionic cholinergic nerves. Virtually all automatically functioning organs in the body, including the brain, are so innervated, therefore, the (side) effects of systemic administration of antimuscarinic drugs are widespread.

These multiple effects of antimuscarinics cause confusion when distinguishing between effects and side effects. For example, suppression of mucosal secretions (a dry mouth) is an undesirable side effect when treating hyperacidity of the stomach but it is a therapeutic objective when these drugs are administered preoperatively. Other side effects include a rapid heart rate, reduction of intestinal motility, reduced ability to sweat, retention of urine, flushing of the skin and dilatation of the pupils. None of these effects or side effects (depending upon the therapeutic goal) are of major consequence but they are sufficiently disturbing to reduce patient compliance. (Brown J H. Atropine, scopolamine and related antimuscarinic drugs. In Goodman and Gilman; 8'th edition: 1990;150–165).

The etiology, pathogenesis and course of the disease(s) of the ANS affecting the bladder follow a sequence that can be discerned both clinically and with ancillary investigations.

It is furthermore known that the group of diseases collectively termed Dysfunctional Bladder has two principal components: Interstitial Cystis (IC) and Neurogenic Spastic Bladder. Said IC is defined by chronic irritative voiding symptoms, usually in middle aged women, sterile and cytologically negative urine, characteristic cystoscopic findings and failure to find objective cause(s). Pathologically, IC in its early stages is characterized by small submucosal haemorrhages surrounded by areas of inflammation and these may progress to scarring which, in some cases, has led to total extirpation of the bladder. Clinically, the condition causes increased frequency of micturition, up to 10–12 times per night (nocturia). Not surprisingly the cost in health expenses, lost productivity and therapy for emotional problems is high, exceeding $400 million per year in the U.S.A. alone. (Interstitial Cystitis. Hanno P, Staskin D R, Krane R J, Wein A J. (edo); Springer-Verlag, New York: 1990).

In contrast to almost all other forms of dysfunctional bladder disease the ANS in IC remains intact: bladder spacticity in this disorder results from inflammatory irritation of submucosal nerve plexus resulting in localized reflexive hyperactivity of the parasympathetic nerves causing spasms of the detrusor muscle, as well as the central sensations of pain and irritation.

Sympathomimetic drugs, either non specifically or selectively, mimic the actions of the sympathetic nervous system, thereby causing relaxation of the detrusor muscle and contraction of sphincter. Drugs such as the natural neurotransmitter, epinephrine, stimulate all 4 subtype receptors: $\beta_1$, $\beta_2$, $\alpha_1$, $\alpha_2$.

Unlike the neurogenic (dysfunctional) bladder wherein the chain, etiology-pathogenesis-clinical course, is well understood, the first link, etiology, remains undiscovered in the dysfunctional bladder of IC; and without an identifiable cause, treatments are empirical rather than logical. In this respect many different aetiologies have been proposed 1) chronic infection caused by some yet-to-be-discovered microorganism; 2) lymphovascular congestion; 3) endocrine abnormalities; 4) autoimmune diseases; 5) defective urothelial layers; 6) neuritis; 7) sympathetic hyperactivity; 8) detrusor hyperactivity; 9) psychoneuroses; 10) IC does not exist! Hypotheses 9) and 10), implying hypochondria and an overactive imagination respectively are not overly popular with the IC patients comprising the "Interstitial Cystitis Society of America", nor are they given serious consideration by the majority of clinicians and investigators involved in this field.

Systemic therapies, suggested and applied in IC, amount to multiples of the above list and, without exception, they have proven either valueless, or induce pathologies more serious than those of IC itself.

Intravesical instillation of certain chemical agents, most notably DMSO (dimethylsulphoxide), have demonstrated benefit in a proportion of patients but relief of symptoms is short lived. It is known a therapy with repeated hydraulic dilatation of the bladder. In particular, a catheter is inserted into the bladder which is then forcibly distended by infusion of fluid from its existing Maximum Bladder Capacity (MBC) to a volume 2–3 times MBC. This painful procedure is performed under general anaesthesia (rarely, regional anaesthesia) and the benefits of the increased bladder capacity last up to about 6 months. A classic example is a patient with a MBC of 80 ml who is dilated up to 200 ml with substantial relief of symptoms for 4 months.

Among the disadvantages encountered by performing this method there are the following:

- general anaesthesia provides the required oblivion but the routine agents used do not induce relaxation of existing detrusor muscle spasm,
- although the degree of distension generally correlates with the duration of symptomatic relief, marked overdistension of a spasming detrusor muscle causes additional haemorrhages and inflammation which, theoretically, summate with the disease process.

It is known by Thiel the iontophoresis of certain heterocyclic compounds in the treatment of bladder cancers (German patent No. DE 38 09 814 C1 and U.S. Pat. No. 5,002,956). Feiring describes "Internal Tissue Medication Permeating Apparatus and Method" (International Patent No. WO 91/16945). Stephen et al. described in U.S. Pat. Nos. 5,222,936; 5,232,441; 5,301,688 intracorporeal iontophoresis, the treatment of schistosomiasis and localization and treatment of bladder cancer.

Gibson et al. (A test for the concentration of electrolytes in cystic fibrosis of the pancreas utilizing pilocarpine by iontophoresis. Pediatrics 1959; 23: 545–549) describe iontophoretic transdermal administration of the cholinergic agonist pilocarpine. Phipps et al. (U.S. Pat. Nos. 4,744,787; 4,747,819) have employed transdermal iontophoresis of the β blocking agent, propranolol, and Haak et al. claimed iontophoretic administration of an antimuscarinic agent, scopolamine, into the skin of the back (U.S. Pat. No. 5,167,616).

It is also known a group of non specific agents acting upon the nervous system, characterized by hydrophilic and hydrophobic domains separated by an intermediate alkyl chain. The hydrophilic group may be a tertiary or a secondary amine and the hydrophobic domain in an aromatic residue. This group of drugs blocks conduction in every type of nerve fiber—sensory, motor, autonomic or somatic—and they are classed as local anaesthetic agents because the sensation of pain in the region supplied by the nerve(s) injected with these drugs is usually the first to disappear. Said agents have been applied clinically for four purposes only: 1) localized administration (which may include various intraspinal techniques) to achieve anaesthesia of designated bodily regions; 2) blockade of the sympathetic nervous system (Smith et al.: U.S. Pat. No. 5,147,294) to achieve relief of chronic pain and improve blood flow to designated regions; 3) systemic administration for treatment of various cardiac arrhythmias; and 4) systemic administration for treatment of ill-defined "central" pain, i.e. pain which arises, or is perceived to arise, within the brain itself. There have been many reports of iontophoretic administration of local anaesthetic agents, usually lidocaine, but only for the purpose of achieving local anaesthesia and Petelenz et al. (U.S. Pat. No. 4,752,785 and Europ. patent No. 0 240 189 B1) have described a technique of reacting the chloride counter ion of lidocaine hydrochloride with certain metallic anodes.

ELECTROMOTIVE DRUG ADMINISTRATION (EMDA)

EMDA comprises at least three important electrokinetic phenomena, which are: iontophoresis, electrophoresis and electroporation.

Iontophoresis is defined as the active transport of ionized molecules into tissues by application of an electric current through a solution containing the ions to be delivered. Quantitative values for the ionic flux (J) may be obtained by applying the Nernst-Planck equation as described by Keister et al. (Keister J C, Kasting G B. Ionic mass transport through a homogeneous membrane in the presence of a uniform electric field. J Membrane Sci 1986; 29; 155–67).

$$J = \frac{-D \cdot \Delta C}{\Delta x} + \frac{D \cdot z \cdot e \cdot E \cdot C}{k \cdot T}$$

where D is the diffusion coefficient, $\Delta C$ is the concentration difference over a distance $\Delta x$, e is the electron charge, z is the valency, k is Boltzman's constant, E the electric field and T the absolute temperature. The first expression on the right side of the equation is Fick's Law of Diffusion and may be described as the passive component. The second expression, the electrical component, shows that the rate of drug administration varies directly as the intensity of the applied electric field. With respect to this invention, it is important to note that, for bladder mucosa (urothelium), the value of the diffusion coefficient approaches zero (D→0), which is in accordance with the physiological function of the bladder. Effectively, this means that passive diffusion of most chemical compounds (especially those that are ionized) into the urothelium is minimal.

Electrophoresis, in accordance with Sibalis (U.S. Pat. No. 4,878,892), describes the transport of solutes associated with bulk movement of water. In an ionic liquid solution, ionophoresis induces transport of water (electro-osmosis) into underlying tissues which, in turn, induces an enhanced penetration of electrolytes down their coulombic gradients, of non electrolytes and even of electrolytes against their coulombic gradients as described by Petelenz et al. (Iontophoresis of dexamethasone: laboratory studies. J. Controlled Rel. 1992; 7(2): 141–148). Usually, iontophoresis dominates electrophoresis in terms of drug administration rates from a pure solution containing the drug in an ionized form. However, if the drug is present in low concentrations (usually $<10^{-2}$ molar) and/or there is a rich admixture of extraneous ions, then the role of electrophoresis in the transport of the drug becomes increasingly important.

Electroporation is a term newly coined by Prausnitz et al. (Transdermal drug delivery by electroporation. Abstract Proceed. Intern. Symp. Control. Rel. Bioact. Mat. 1992;19.) and is used to describe a phenomenon known for many years: it was described by Jung et al. in 1983 (Conformational requirements for the potential dependent pore formation of the peptide antibiotics alamethicin, suzukacillin and trichotoxin. In: Spach G ed. Physical Chemistry of Transmembrane Ion Motion. New York: Elsevier; 1983). Application of an electric field causes an increase in the permeability of biological membranes and thus there is increased transport of drugs down concentration gradients because the value of the diffusion coefficient (D) has been increased.

Thus, the three electrokinetic phenomena, iontophoresis, electrophoresis and electroporation are all involved in EMDA within the bladder. As stated herein above, iontophoresis is usually predominant when the drug ion to be administered is of the same polarity as the applied electrode but, if the concentration of the drug ion (and its counterion) is too low to conduct the applied electric current effectively, then problems such as polarization and hydrolysis of water become manifest. To counter these undesirable effects, additional extraneous electrolytes (often in the form of buffers)

are usually added to the drug solution. These same electrolytes then act as charge competitors, reducing the iontophoretic rate of drug delivery while increasing electrophoretic transport rates, especially if these additional ions are carefully selected as described by Sibalis (U.S. Pat. No. 4,878,892). Extraneous ions are an inevitable accompaniment of EMDA within the bladder because of the continuous entry of electrolyte-rich urine, so that electrophoresis will inevitably be involved. Excepting the specific conditions described by Prausnitz et al., the contribution supplied by electroporation to EMDA is generally unknown and it is only mentioned in this submission for the sake of completeness.

It is well known in the art the use of catheters in order to drainage the bladder, when lesion of the ANS gives rise to a neurogenic bladder. The catheters may be inserted into the bladder via the urethra or through suprapubic abdominal incision. Continuous catheter drainage is the usual technique, which means that, although the catheters are changed periodically, they are resident within the bladder on a permanent basis. As stated herein before, the clinical consequences of this situation are grave.

With an incidence approaching 100%, pathogenic micro-organisms gain access to the bladder, either down the lumen of the catheter or, more importantly, between the external walls of the catheter and the distorted (and therefore "defenceless") surrounding tissues: the urethra or the incision in the abdominal wall. Once within the bladder, the micro-organisms multiply within "privileged" sites provided by the intravesical portion of the catheter and rapidly become resistant to most, if not all, antimicrobial agents. Moreover, the catheter constantly irritates and inflames the bladder wall so that, over time, the combination of chronic infection and mechanical irritation causes scarring and contraction of the bladder, damage to the ureters and consequent upper urinary tract obstruction and eventually kidney failure. Many patients with permanent bladder catheter are treated with artificial kidneys because of kidney failure and countless numbers have died of overwhelming infections caused by the resistant microorganisms residing in a catheterized bladder.

Recalcitrant, antimicrobial-resistant infection and all the subsequent sequelae remain the most prominent problems associated with a neurogenic bladder to this day.

There have been numerous attempts to ameliorate the side effects described herein above. Intermittent clamping of an indwelling catheter occludes the intraluminal pathway to infection for most of the time and, with accumulation of urine in the bladder, traumatic damage by the tip of the catheter is less likely. Unfortunately the detrusor contractions of a spastic bladder cause voiding of urine around the catheter. Therefore, patient compliance is uncertain as most individuals prefer to remain "dry" with continuous drainage rather than "wet" with intermittent clamping.

According to Donovan et al. (Bacturia during intermittent catheterization following spinal cord injury. Arch. Phys. Med. Rehabil. 1978; 59: 351) and Rhome et al. (Urinary tract infections occurring in recently injured spinal cord patients. J. Urol. 1979; 123: 669), intermittent catheterization causes less infection than chronic, indwelling catheters do.

Nevertheless, with spastic bladders of capacity 50–100 ml, intermittent catheterization becomes an almost meaningless term: with average daily volumes of urine varying 1–3 liters, it would be necessary to insert the catheter 10–30 times day and night over a 24 hour period in order to avoid detrusor expulsion of urine at inconvenient times.

It is also known that systemic administration of anticholinergic drugs reverses some of the detrusor hypertonicity but the ultimate value of these agents so administered is problematic because side effects, predominantly dry mouth and constipation, result in poor patient compliance.

It is also known from Brendler et al. (Topical oxybutynin for relaxation of dysfunctional bladder. J. Urol. 1988; 141: 1350) and Greenfield et al. (The use of oxybutynin chloride in children with neurogenic bladder. J. Urol. 1991; 46: 537) that intravesical administration of anticholinergic drugs is more effective than the systemic route and that there are fewer side effects. However, adjustment of dosages for this passive intravesical method of administration is difficult because intact bladder mucosa has a very low diffusion coefficient but, given enough time and sufficiently high concentration within the bladder cavity, some drug will diffuse into the bladder wall:

$$J = -D\Delta C/\Delta x.$$

The first problem arises with the rate of urine production which may vary 200% or more in the same individual, depending upon a variety of factors such as the amount of fluid intake, ambient temperature, physical activity and many more: thus, the concentration gradient ($\Delta C/\Delta x$), upon which the rate of diffusion depends, does not yield a predictable value with respect to the concentration of drug instilled into the bladder cavity. Secondly, because of the relative impermeability of intact urothelium, high concentrations (and therefore quantities) are required within the bladder cavity to achieve therapeutic levels in the bladder wall; if the urothelium is damaged, as it is often the case with a catheterized, neurogenic bladder, there will occur rapid systemic absorption of the drug through localized, denuded areas of bladder wall leading to side effects, possibly severe.

Griffith et al. (Tissue-bonded iontophoretic cystostomy: conceptual and experimental considerations. J. Endourology 1993; 7 (2): 169–177; and U.S. Pat. No. 5,234,408) described that suprapubic catheters bonded to the abdominal wall, through which they emerge, are less likely to transmit infections into the bladder: the appropriate lenght of surface of the catheter is so modified that dense fibrous (scar) tissue forms a living, impermeable seal between the abdominal wall and the catheter, preventing micro-organisms tracking external to the catheter and into the bladder. Theoretically, if the catheter were capped, and released only 3–4 times daily to empty the bladder, the chances of infectious organisms entering via the only possible route, the lumen of the catheter, are also reduced. Unfortunately, the now familiar spastic bladder of capacity 50–100 ml would require uncapping 10–30 times daily; the authors therefore suggest remedial intravesical instillation of anticholinergic agents, the limitations whereof when administered by passive diffusion have been described herein above.

The term "iontophoretic", as used by Griffith et al., illustrates the uncertainty in the nomenclature within this particular therapeutic field. These investigators define iontophoresis as " . . . the use of direct electrical current for therapeutic purposes". And they employ the technique described by Davis et al. (U.S. Pat. No. 4,411,648; and: Bacterial fungal killing by iontophoresis with long lived electrodes. Antimicrob. Agents Chemoter 1991; 35: 2131) wherein both positive and negative electrodes, attached to the same power source, are inserted into the bladder catheter, or via the catheter into the bladder, and the urine or an instilled electrolyte solution completes the circuit so that a small (microamperes) direct current may be applied. For reasons not fully clarified, these small currents result in substantial killing of micro-organisms over 6–8 hours even when inert (not oxidized) electrodes such as carbon or platinum are used. Nevertheless, it is very important to note that iontophoresis, as defined by Griffith et al. with both positive and negative electrodes within the bladder cavity, will not result in electromotive administration of drugs into the bladder wall. Indeed polarization effects will result in the positively charged anticholinergic drugs clustering around the negative electrode and transport into the bladder wall will be impeded.

SUMMARY OF THE INVENTION

It is a principal object of this invention to provide an improved method of controlling Dysfunctional Bladder Symptomatology associated with the pathological disorders of Interstitial Cystitis and Spastic Neurogenic Bladder.

It is another object of this invention to induce relaxation of a hypertonic detrusor muscle within a bladder wall by EMDA, avoiding the principal side effects of oral/systemic administration.

A further object of this invention is to achieve more profound and more prolonged relaxation of the detrusor muscle of the bladder in order to obtain a long-term relief of pain.

Yet another object of the invention is to take advantage of the induced detrusor relaxation and to dilate the bladder by means of Active Hydraulic Dilatation or Passive Hydraulic Dilatation.

Other objects of the present invention will become manifest from a consideration of the specification, accompanying drawings and appended claims.

With the foregoing and other objects in view, while taking the aforementioned boundary conditions into consideration, there is provided, in accordance with the invention, a method of treating dysfunctional bladder syndromes by Electromotive Drug Administration of intravesically instilled drug into a bladder wall, said method comprising the steps of:

a) inserting a catheter via a urethra into a bladder and draining said bladder of the urinary contents.

b) administering into said bladder via said catheter an electrically conductive aqueous solution of at least one drug which causes relaxation of the detrusor muscle, c) inserting into said catheter a tubular anodic electrode connected to an external controllable power source, so that the internal tip of said electrode resides within that section of said catheter which is within the bladder cavity, d) placing a cathodic electrode in contact with an adapted skin location, said cathodic electrode being also connected to said external power source, e) supplying said electrodes with an electric current from said power source, f) instituting hydraulic dilatation of said bladder.

According to one aspect of the present invention, the dilatation of said bladder is achieved by active pressurized intravesical infusion of a solution through said catheter, preferably to maximum intravesical volume of 700 ml. Said infused solution is preferably an aqueous sterile and apyrogenic solution, more preferably a sterile physiological electrolyte solution.

According to another aspect of the present invention, the dilatation of said bladder is achieved by the promotion of passive hydraulic dilatation of the bladder, obtained by clamping the catheter inserted according to the aforementioned step a), thereby trapping inflowing urine within the bladder cavity and distending said bladder preferably to maximum intravesical volume of 700 ml.

Active Hydraulic Dilatation is defined as the intravesical infusion of fluids for the purpose of achieving significant dysfunctional bladder dilatation within a specific time of one hour or less.

Passive Hydraulic Dilatation is defined as the slow dilatation of the dysfunctional bladder achieved by the natural influx of urine (average flow rate 1 ml/min) over a period extending to 8 hours.

At least one said drug which causes relaxation of the detrusor muscle is water soluble, in the form of ionized salts and all drug ions are positively charged. Moreover, the total quantity of any drug administered through intravesical infusion does not exceed the total daily dose of the same drug used in conventional systemic administration, in order to avoid possible side effects. At least one said drug is preferably administered in a conductive aqueous physiological solution, having preferably a volume of 50 to 150 ml, more preferably of 100 ml.

The intravesical electrode used in the present invention is anodic.

In accordance with a further feature of the invention, at least one said drug which causes relaxation of the detrusor muscle comprises at least a local anaesthetic agent. In this particular way it is possible to provide an anaesthetic drug to the bladder with the purpose of achieving relaxation of the muscle for a time sufficient to institute an active hydraulic dilatation of the bladder. Preferably said local anaesthetic drug is selected from the group comprising lidocaine, mepivacaine, bupivacaine and a mixture thereof. More preferably said local anaesthetic drug is administered in the form of an aqueous solution at a concentration of 0.3 to 2% by weight/volume.

In accordance with a further feature of the invention, a sympathomimetic drug is added to said aqueous solution of said local anaesthetic drug and administered into said bladder in order to enhance the detrusor muscle relaxation. Preferably, said sympathomimetic drug is selected from the group comprising epinephrine and ephedrine.

In accordance with another feature of the invention at least one said drug which causes relaxation of the detrusor muscle comprises a local anaesthetic drug, a sympathomimetic agent and an antimuscarinic agent. This drug mixture allows a more profound muscle relaxation and is administered in order to allow an active pressurized intravesical infusion of a solution in order to obtain a large bladder dilatation. Preferably said antimuscarinic agent is selected from the group comprising atropine, scopolamine, homatropine, dicyclomine, oxyphencyclamine, flavoxate, oxybutynin, methantheline, methscopolamine, octatrophine, parapenzolate, pentapiperide, pipenzolate, prifinium, propanteline, butylscopolamine, tiemonium, xenytropium, dihexyverine, propiverine, terodyline, diphemanile, emepronium, hexacyclium, fentonium, isopropamide, trospium and mixtures thereof.

More preferably said antimuscarinic agent is administered in the form of an aqueous solution at a concentration of 0.001% to 0.2% by weight/volume and still more preferably it is administered in the form of a physiological electrolyte solution of osmolarity range of 150 to 310 milliosmols. According to a particular embodiment, said antimuscarinic agent is administered in the form of a sodium or potassium citrate solution and more preferably at a concentration of 1.0% to 3.0% by weight. Since inflamed bladder tends to bleed, said citrate solution exhibits an effective localized anticoagulant effect, avoiding that blood clots block catheter drainage of the bladder.

According to another embodiment of the present invention, said passive dilatation of the bladder is achieved by administering an electrically conductive aqueous solution of at least a drug which causes relaxation of the detrusor muscle, preferably comprising an antimuscarinic agent, preferably selected from the group previously listed.

Preferably said antimuscarinic agent is administered in the form of an aqueous solution at a concentration of 0.001 to 0.2% weight/volume, more preferably as a physiological electrolyte solution of osmolarity range of 150 to 310 milliosmols. According to another embodiment, said antimuscarinic agent is administered in the form of a sodium or potassium citrate solution, preferably at a concentration of 1.0% to 3.0% by weight.

In accordance with an additional feature of the invention, at least one said drug which causes relaxation of the detrusor muscle comprises a local anaesthetic drug and an antimuscarinic agent. Preferably said anaesthetic drug is selected from the aforementioned group and more preferably it is administered in the form of an aqueous solution at a concentration of 0.3 to 2.0% by weight/volume.

In accordance with still another feature of the present invention, at least one said drug which causes relaxation of the detrusor muscle, in order to achieve said passive hydraulic dilatation of the bladder, comprises an association of a local anaesthetic drug, an antimuscarinic agent and a sympathomimetic drug.

In accordance with another feature of the invention, the intensity of the electric current supplied from the power source to the electrodes is preferably of 10 mA to 30 mA and it is a pulsating current or a constant current.

In a preferred embodiment said electric current is supplied for time periods ranging from 10 to 60 minutes.

Electromotive administration of the drugs, combined with hydraulic dilatation of dysfunctional bladders, according to the present invention, results in relief of detrusor spasm for a duration far exceeding the duration of action of the drugs themselves.

Moreover the method of treatment according to the present invention allows to reduce the incidence of morbidity and mortality resulting from the drainage of the neurogenic bladder performed by known techniques. By providing the method according to the invention it is therefore avoided the incidence of morbidity and mortality which are correlated with the dwell times of removable catheter or the number of uncappings of tissue-bonded catheter. Furthermore by performing the EMDA according to the invention, there are minor drawbacks associated with conventional modes of administration of pharmacological agents.

TABLE I summarizes the drugs which are preferably used in performing the method according to the present invention, in order to achieve relaxation of the detrusor muscle.

TABLE I

DRUGS WICH CAUSE RELAXATION OF THE DETRUSOR MUSCLE

| Antimuscarinic | | Sympathomimetic | | Local |
| --- | --- | --- | --- | --- |
| Tertiary Amines | Quaternary Amines | $\beta_2$ Agonists | $\alpha_1$ Agonists | Anaesthetic Drugs |
| Atropine | Trospium | Epinephrine | Epinephrine | Lidocaine |
| Scopolamine | Methantheline | Ephedrine | Ephedrine | Mepivacaine |
| Homatropine | Methscopolamine | Metaproternol | | Bupivacaine |
| Dicyclomine | Octatropine | Terbutaline | | |
| Oxyphencyclamine | Parapenzotate | Perbutenol | | |
| Dihexyverine | Pentapiperide | Bitolterol | | |
| Propiverine | Pipenzolate | | | |
| Terodyline | Prifinium | | | |
| Flavoxate | Propantheline | | | |
| Oxybutynin | Butylscopolamine | | | |
| | Tiemonium | | | |
| | Xenytropium | | | |
| | Diphemanile | | | |
| | Emepromium | | | |
| | Hexacyclium | | | |
| | Fentonium | | | |
| | Isopropamide | | | |

BRIEF DESCRIPTION OF THE DRAWINGS

The method of treatment according to the present invention, together with additional objects and advantages thereof, will be best understood from the following description of specific embodiments when read in connection with the accompanying drawings, in which.

DESCRIPTION OF THE PREFERRED EMBODIMENTS

Figure 1:
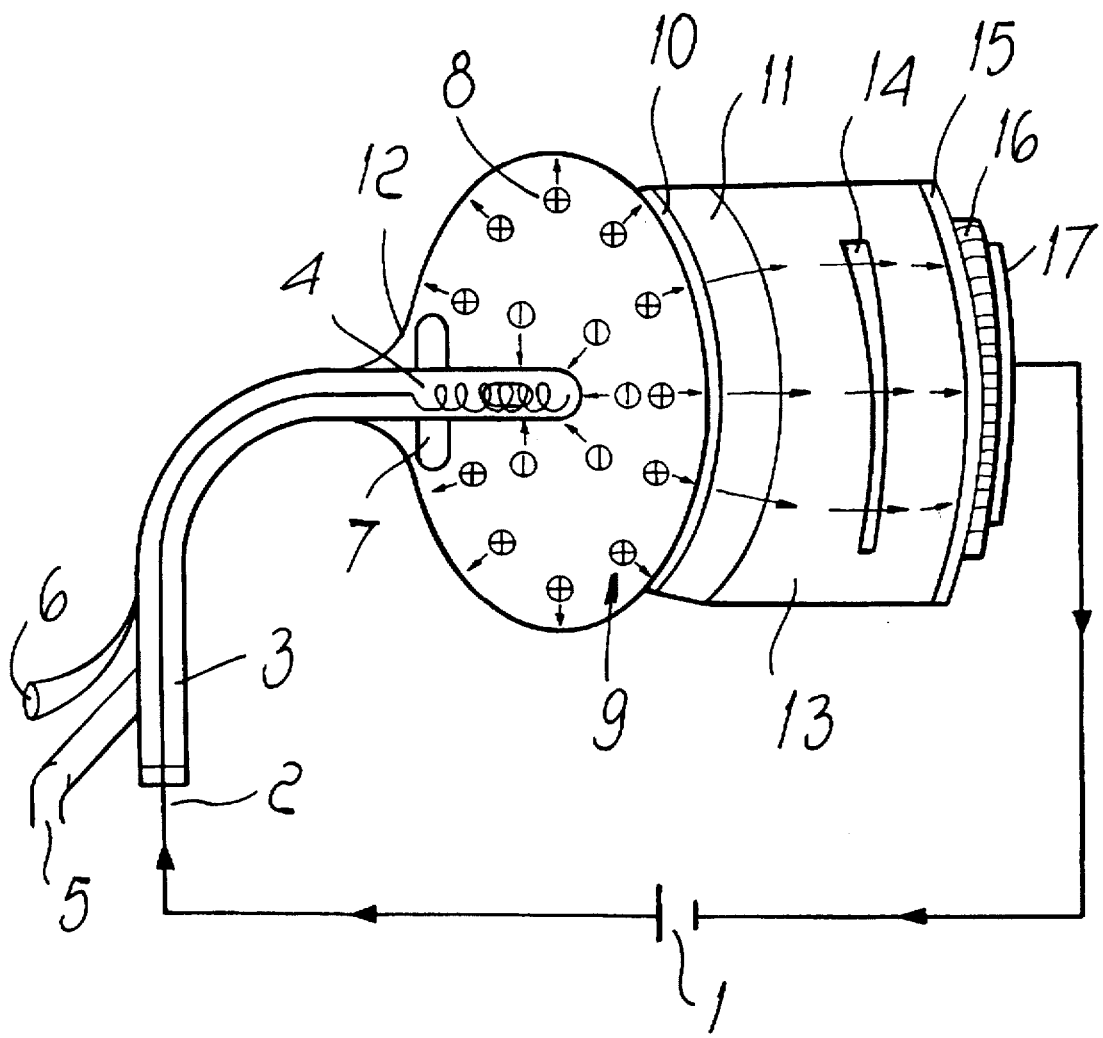
FIG. 1 is a schematic representation of current flow from a spiral intravesical electrode to the dispersive skin electrode, according to the present invention.

With reference to the drawings and in particular to FIG. 1 thereof, there is shown an overall schematic view of the preferred embodiment of the present invention. The illustrated power source 1 is electrically connected to an insulated, conductive tubular member 2 within an urethral catheter 3 and terminating in an uninsulated spiral section 4 in close apposition to the intravesical drainage holes of the catheter. Desirably, the urinary catheter may be one of several readily available urethral or suprapubic catheters, e.g. a FOLEY-type catheter, and will provide additional ports for intravesical instillation of fluids 5 and for insufflation of air 6 to inflate the balloon 7. Aqueous solutions of the desired drugs 9 in volumes ranging approximately from 50 ml–200 ml are infused into the bladder 8; importantly, all drugs are in the form of positively charged ions. Upon application of an electric current from the power source 1, drug ions 9 are repelled into and through the urothelium 10 lining the bladder wall and thence into the detrusor muscle 11 and the internal sphincter 12, where they will attach to their specific receptors. The general path of the electric current will continue through body tissues 13 surrounding the bladder, predominantly bypassing highly electrically resistive structures such as nerves 14; and then through the skin 15, the overlying external layer of a conductive gel 16 and the external (dispersive) electrode 17 which is electrically connected to the negative pole of the power source.

Figure 2:
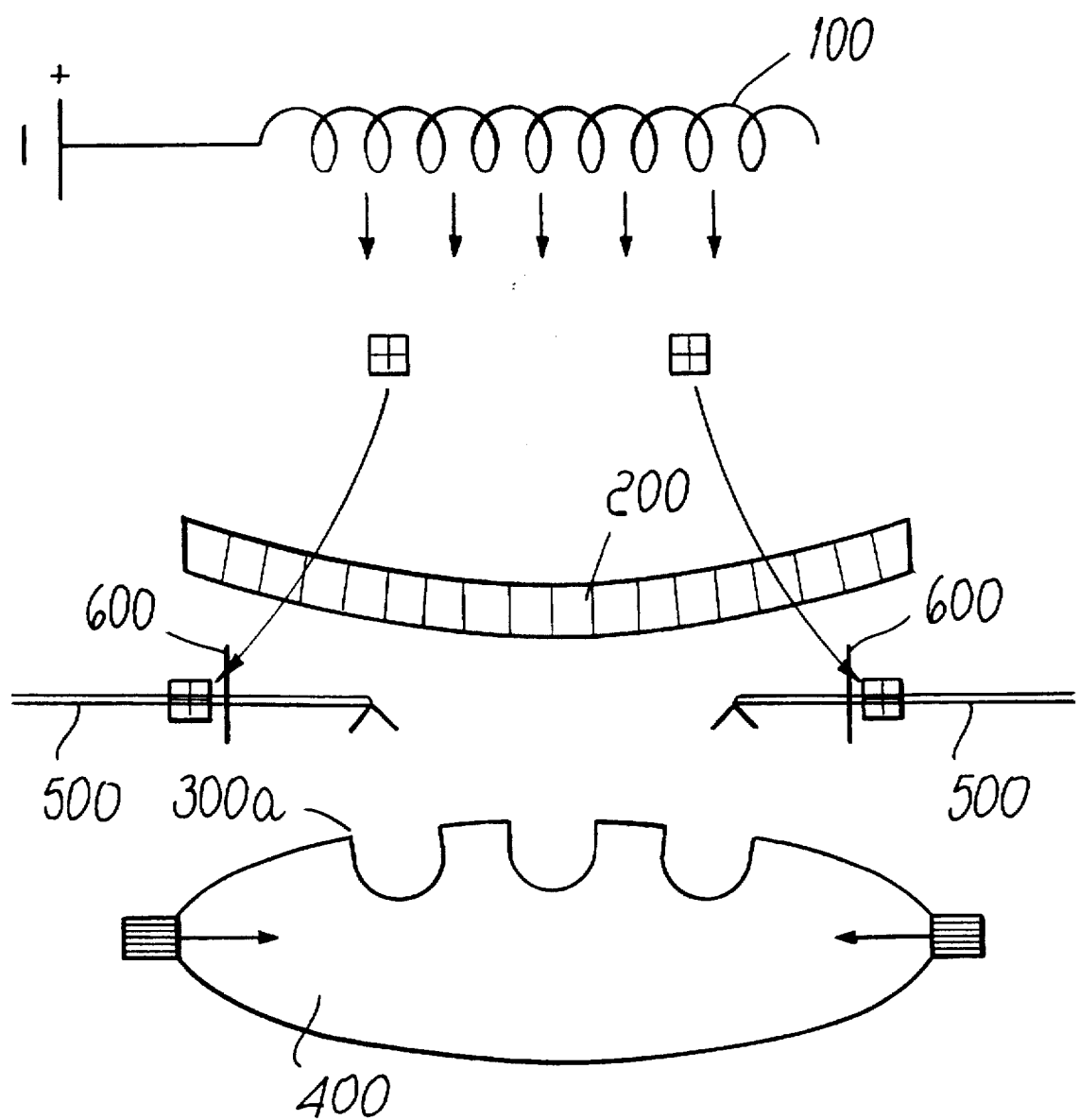
FIG. 2 is a schematic representation of the inhibitory action of a local anaesthetic drug on a parasympathetic nerve fiber according to the present invention.

FIG. 2 shows a schematic representation of electromotive administration of a local anaesthetic drug for treatment of a spastic bladder in accordance with the present invention. The positively charged electrode 100 repels the positively local anaesthetic ions through the urothelium 200 and into specific sites 600, the sodium-potassium channels, along the axons of parasympathetic nerves 500 where said local anaesthetic drugs induce a reversible blockage of conduction along said nerves.

Production and release of acetylcholine at the parasympathetic nerve terminals are interrupted and the spastic detrusor muscle 400, deprived of its prime native stimulus to its cholinergic receptors 300a, relaxes. The duration of action of the local anaesthetic drug depends on the particular drug selected ("long acting", "short acting") and on the blood supply to the region: the blood flow rate and duration of action of the drug are inverse functions of one another.

Figure 3:
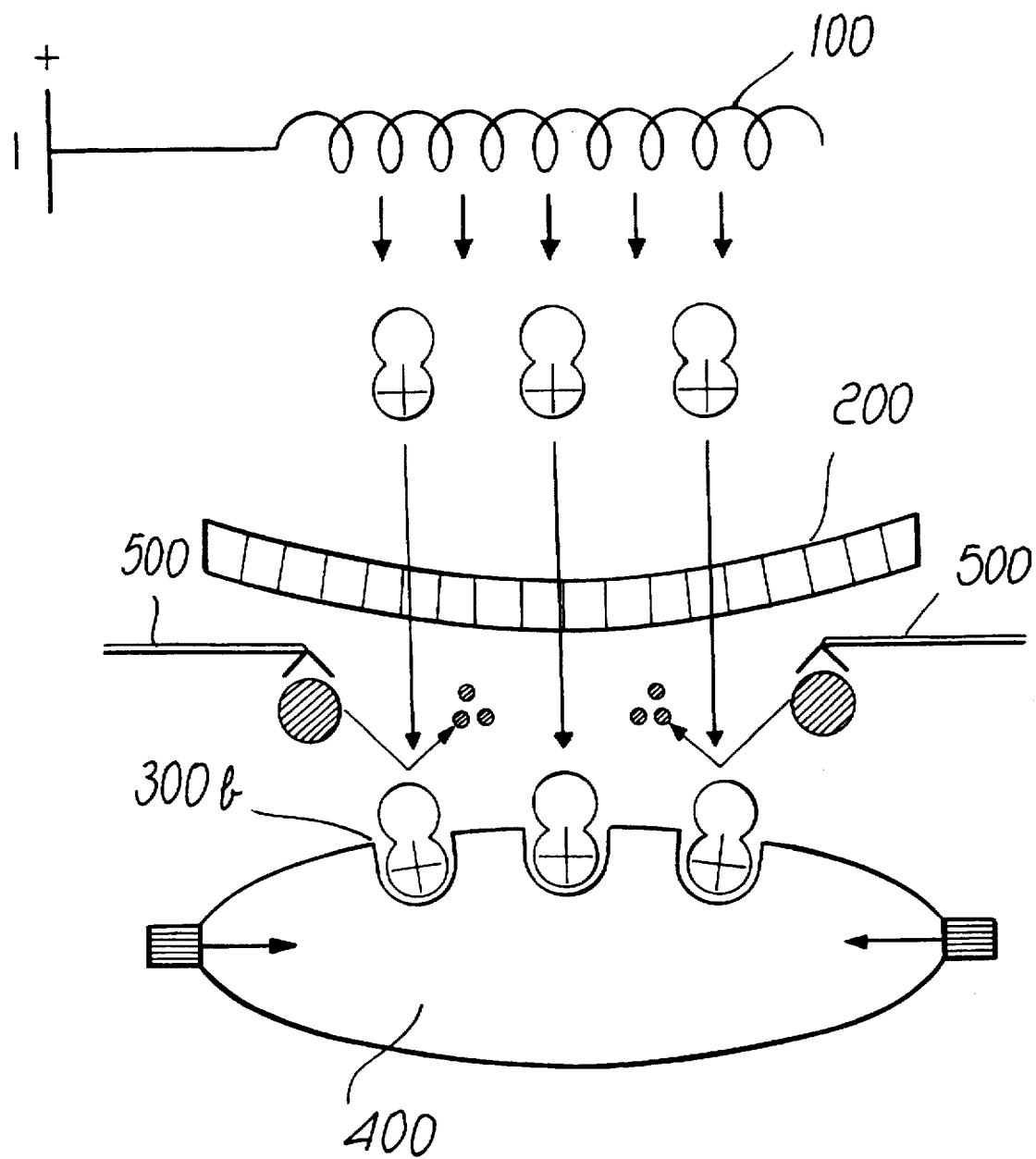
FIG. 3 is a schematic representation of the antagonist action of an antimuscarinic drug according to the present invention.

In FIG. 3 there is depicted a schematic representation of electromotive administration of an antimuscarinic drug for treatment of a spastic bladder in accordance with the present invention. The positively charged intravesical electrode 100 repels positively charged antimuscarinic ions through the urothelium 200 into the receptor sites 300b of the detrusor muscle 400. The chemistry of these drug ions is such that they combine with said receptor sites but their spatial configuration is such that this combination cannot effect muscle contraction. The slow degradation of antimuscarinic drugs locked into detrusor muscle receptor sites constitutes competitive blocking of acetylcholine, released from parasympathetic nerve terminals 500 and rapidly inactivated by cholinesterase enzyme. The detrusor muscle, deprived of its prime native stimulus to contract, then relaxes for as long as the duration of action of the antimuscarinic drug being employed.

EXAMPLES

The following examples are only illustrative of the present invention. Several modifications and alternatives may be devised by those skilled in the art without departing from the spirit and the scope of the present invention.

IC Bladder

TABLE II provides a brief summary of 15 IC patients treated according to the method of the present invention.

TABLE II

SUMMARY OF 15 PATIENTS WITH INTERSTITIAL CYSTITIS (IC) TREATED BY BLADDER DILATATION FOLLOWING INTRAVESICAL ELECTROMOTIVE ADMINISTRATION OF LIDOCAINE AND EPINEPHRINE

| Center No. | Patients | Sex | Mean pre-op. Bladder Capacity (ml) | Mean post-op. Bladder Capacity (ml) |
|---|---|---|---|---|
| 1 | 2 | 2 F | 80 | 490 |
| 2 | 1 | 1 M | 90 | 430 |
| 3 | 2 | 2 F | 85 | 510 |
| 4 | 2 | 1 M/1 F | 100 | 630 |
| 5 | 2 | 2 F | 100 | 510 |
| 6 | 1 | 1 F | 85 | 470 |
| 7 | 1 | 1 F | 80 | 390 |
| 8 | 2 | 2 F | 70 | 360 |
| 9 | 2 | 2 F | 75 | 370 |
| | | MEAN | 84 | 462 |

CURRENT: 13 mA average (max 14 mA – min 12 mA)
TIME: 45 minutes
DRUGS: 1% Lidocaine, 1:100.000 Epinephrine
COMMENTS
- All patients with diagnosed IC.
- No pre-operative or intra-operative medications (sedative-analgesics) were administered.
- Side effects: the patients noted tingling at the site of skin electrode as well as hyperaemia in the same place at the end of the therapy.

The results are as follows:
1. An approximate 5 fold increase in the average intravesical volume was achieved: 84 ml→462 ml.
2. This increase in volume was achieved without a clinically significant rise in intravesical pressure (an IC patient is quick in drawing attention to the pain associated with an increasing intravesical pressure).

Further advantages in performing the method of the invention include an alert patient supplying feedback during dilatation, no recovery room monitoring required and no hospital bed required (Fontanella U A, Rossi C A, Stephen R L. Iontophoretic Local Anaesthesia for Bladder Dilatation in the Treatment of Interstitial Cystitis. British J. Urology June 1992 69(6) 662–663).

Corresponding results issuing from bladder dilatation under general anaesthesia are a 2–3 fold increase in bladder volume and an average symptom-free period of 3–4 months. Thus the investigators on this application realized that relaxation of the detrusor muscle by local anaesthetic drugs allowed a greater hydraulic dilatation and that this effect conferred improved clinical results, because, as stated herein above, the greater the dilatation achieved without concomitant haemorrhages, the longer the duration of relief.

The embodiment of the present invention according to which local anaesthetic drugs are used, empathized the innovative use of said drugs, in order to achieve the relaxation of any smooth muscle and in particular the bladder detrusor relaxation, for therapeutic purposes.

Moreover, according to another aspect, the present invention provides a useful means to investigate at least one of the hypotheses on the etiology of IC: detrusor hyperactivity.
Spastic, Neurogenic Bladder TABLE III summarizes the results of EMDA treatments of five patients with spastic bladders resulting from either spinal cord transection or Spina Bifida. The three drugs used were trospium, butyl scopolamine and oxybutinin, all antimuscarinic agents.

TABLE III

FIVE PATIENTS WITH SPASTIC NEUROGENIC BLADDERS TREATED WITH EMDA OF INTRAVESICAL ANTIMUSCARINIC DRUGS

| PATIENT | | | | URODYNAMIC MEASUREMENTS | | | |
|---|---|---|---|---|---|---|---|
| | | | | Pre-treatment | | Post-treatment | |
| No. | Age | Sex | DRUG | **Max. Bladder Capacity (ml) | **Max. detrusor Pressure (cm $H_2O$) | Max. Bladder Capacity (ml) | Max. detrusor Pressure (cm $H_2O$) |
| 1 | 26 | F | But. scopolam.* | 140 | 120 | 220 | 100 |
| 2 | 13 | M | Trospium | 80 | 80 | 250 | 80 |
| 3 | 24 | M | Trospium | 320 | 70 | 500 | 50 |
| 4 | 32 | F | But. scopolam.* | 40 | 110 | 160 | 80 |
| 5 | 55 | F | Oxybutynin | 30 | 40 | 200 | 40 |
| | | | MEAN | 122 | 84 | 266 | 70 |

*But. scopalam. = Butylscopolamine
**Measured while patient was voiding urine
EMDA: 10–15 mA; 15–20 minutes By performing the treatment, the fact is empathized that:

1. The average maximum bladder capacity is more than doubled from 122 ml to 226 ml.
2. This increase in bladder capacity was achieved without an increase in the average detrusor (intravesical) pressure, which in fact was slightly lower (70 cm $H_2O$ vs. 84 cm $H_2O$).
3. The duration of bladder relaxation averaged approximately to 6 hours.

A typical example of Active Hydraulic Dilatation is in a patient undergoing EMDA of a 100 ml volume of a drug solution, according to the invention and infusion of 20 ml increments at 2 minute intervals. After 40 minutes the bladder contains:

```
100 ml drug solution +
400 ml infused fluid +
 40 ml (approx.) of urine
─────────────────────
540 ml total
``` which represents an approximate 5 fold increase in the original MBC of 100 ml.

Similarly, Passive Hydraulic Dilatation over an 8 hour interval with a urinary influx of 1 ml/min will result in the original bladder volume increasing from 100 ml to 580 ml.

The absolute precondition for the examples provided hereinbelow is that the detrusor muscle must be relaxed during dilatation so as to achieve maximum dilatation with minimal-to-absent traumatic damage.

Active Hydraulic Dilatation

1. Short procedures (<30 min): Intravesical EMDA of any local anaesthetic agent.
2. Intermediate procedures (30–60 min): Intravesical EMDA of mepivacaine and bupivacaine.
3. Long procedures (60–90 min): Intravesical EMDA of any local anaesthetic agent with the addition of the vasoconstrictive agent, epinephrine.
4. For post-treatment prolonged detrusor relaxation: Any local anaesthetic agent with an antimuscarinic drug and with or without the vasoconstrictor, epinephrine.

Passive Hydraulic Dilatation

1. All such procedures are envisaged as lasting over a time range of 3–8 hours.
2. Therefore, the drugs selected for initial intravesical instillation and EMDA are:
   a. An antimuscarinic drug in a physiological electrolyte or citrate solution.
   b. An antimuscarinic drug and a local anaesthetic drug in distilled water.
   c. An antimuscarinic drug with a local anaesthetic agent and the vasoconstrictor, epinephrine.

EMDA (electric current) is applied for up to 60 minutes: influx of urinary ions into the bladder continually attenuates the effectiveness of this method of drug delivery and, after approximately one hour, predictive drug delivery rates are almost meaningless. Therefore, the duration of detrusor relaxation depends largely upon the duration of the therapeutic effect of each particular drug. Judicious EMDA of lidocaine (short acting), mepivacaine (intermediate) and bupivacaine (long acting) with and without epinephrine provide detrusor relaxation ranging 20 min–3 hours. As stated hereinabove, the duration of detrusor relaxation achieved with EMDA of 3 antimuscarinic drugs (Table III) was approximately 6 hours. The combination of a local anaesthetic and an antimuscarinic drug will at the least be additive, and possibly synergistic (different target sites) leading to additional duration of detrusor relaxation, an effect that can be further enhanced by the presence of a vasoconstrictor agent such as epinephrine.

What is claimed is:

1. A method of treating dysfunctional bladder syndromes by Electromotive Drug Administration of intravesically instilled drug into a bladder wall, said method comprising the steps of:
   a) inserting a catheter via a urethra into a bladder and draining said bladder of urinary contents,
   b) administering into said bladder via said catheter an electrically conductive aqueous solution comprising at least a local anaesthetic agent and an antimuscarinic agent to achieve both analgesia and relaxation of the detrusor muscle,
   c) inserting into said catheter a tubular anodic electrode connected to an external controllable power source, so that the internal tip of said electrode resides within that section of said catheter which is within the bladder cavity,
   d) placing in contact with an adapted skin location a cathodic electrode also connected to said external power source, e) supplying an electrical current from said power source to said electrodes, f) instituting a progressive active hydraulic dilatation of said bladder by infusing, portionwise, through said catheter, a solution to substantially achieve its maximum intravesical volume.

2. A method according to claim 1, wherein the solution of step f) is an electrically conductive aqueous solution including a local anaesthetic agent at a concentration of 0.3 to 2% by weight/volume.

3. A method according to claim 1, wherein said local anaesthetic agent is selected from the group consisting of lidocaine, mepivacaine, bupivacaine, and mixtures thereof.

4. A method according to claim 3, wherein said local anaesthetic agent is administered in the form of an aqueous solution at a concentration of 0.3% to 2.0% by weight/volume.

5. A method according to claim 1, wherein said electrically conductive aqueous solution further comprises a sympathomimetic agent.

6. A method according to claim 5, wherein said sympathomimethic agent is selected from the group consisting of epinephrine, ephedrine and mixture thereof.

7. A method according to claim 1, wherein a volume of from 50 to 150 ml of said electrically conductive aqueous solution is administered and an electrical current having an intensity of from 10 mA to 30 mA is supplied.

8. A method of treating dysfunctional bladder syndromes by Electromotive Drug Administration of intravesically instilled drug into a bladder wall, said method comprising the steps of:

a) inserting a catheter via a urethra into a bladder and draining said bladder of urinary contents, b) administering into said bladder via said catheter an electrically conductive aqueous solution of at least one drug which causes relaxation of the detrusor muscle, c) inserting into said catheter a tubular anodic electrode connected to an external controllable power source, so that the internal tip of said electrode resides within that section of said catheter which is within the bladder cavity, d) placing in contact with an adapted skin location a cathodic electrode also connected to said external power source, e) supplying an electrical current from said power source to said electrodes, f) instituting a passive hydraulic dilatation of said bladder by clamping said catheter and thereby trapping inflowing urine within the bladder cavity and distending said bladder to substantially achieve its maximum intravesical volume.

9. A method according to claim 8, wherein the at least one drug which causes relaxation of the detrusor muscle comprises an antimuscarinic agent.

10. A method according to claim 9, wherein said antimuscarinic agent is selected from the group consisting of atropine, scopolamine, homatropine, dicyclomine, oxyphencyclamine, flavoxate, oxybutynin, methantheline, methscopolamine, octatrophine, parapenzolate, pentapiperide, pipenzolate, prifinium, propanteline, butylscopolamine, tiemonium, xenytropium, dihexyverine, propiverine, terodyline, diphemanile, emepronium, hexacyclium, fentonium, isopropamide, trospium, and mixtures thereof.

11. A method according to claim 9, wherein said antimuscarinic agent is administered in the form of an aqueous solution at a concentration of 0.001% to 0.2% by weight/volume.

12. A method according to claim 9, wherein said antimuscarinic agent is administered in the form of a sodium or potassium citrate solution at a concentration of 1.0% to 3.0% by weight.

13. A method according to claim 8, wherein the at least one drug which causes relaxation of the detrusor muscle is administered in the form of a physiological electrolyte solution having an osmolarity of from 150 to 310 milliosmols.

14. A method according to claim 8, wherein the at least one said drug which causes relaxation of the detrusor muscle comprises a local anaesthetic agent and an antimuscarinic agent.

15. A method according to claim 8, wherein a volume of from 50 to 150 ml of said electrically conductive aqueous solution is administered and an electrical current having an intensity of from 10 mA to 30 mA is supplied.

* * * * *